United States Patent [19]

Kouba et al.

[11] Patent Number: 4,656,297

[45] Date of Patent: Apr. 7, 1987

[54] COPRODUCTION OF BUTANEDIOL AND TETRAHYDROFURAN AND THEIR SUBSEQUENT SEPARATION FROM THE REACTION PRODUCT MIXTURE

[75] Inventors: Jay K. Kouba, Downers Grove; Robert B. Snyder, Naperville, both of Ill.

[73] Assignee: Amoco Corporation, Chicago, Ill.

[21] Appl. No.: 830,706

[22] Filed: Feb. 18, 1986

Related U.S. Application Data

[63] Continuation-in-part of Ser. No. 710,016, Mar. 11, 1985, Pat. No. 4,613,707.

[51] Int. Cl.$^4$ ............... C07D 307/08; C07C 27/06
[52] U.S. Cl. ............................. 549/508; 568/864; 568/885
[58] Field of Search ................ 549/508; 568/864, 885

[56] References Cited

U.S. PATENT DOCUMENTS

| | | | |
|---|---|---|---|
| 2,091,800 | 8/1937 | Adkins et al. | 568/864 |
| 2,772,291 | 11/1956 | McShane et al. | 260/343.6 |
| 2,772,292 | 11/1956 | McShane et al. | 260/343.6 |
| 2,772,293 | 11/1956 | Gilbert et al. | 260/343.6 |
| 4,048,196 | 9/1977 | Broecker et al. | 260/346.11 |
| 4,172,961 | 10/1979 | Henery et al. | 568/864 |
| 4,268,695 | 5/1981 | Lange et al. | 568/864 |
| 4,301,077 | 11/1981 | Pesa et al. | 260/346.11 |
| 4,332,645 | 6/1982 | Mueller et al. | 203/75 |
| 4,361,710 | 11/1982 | Weitz et al. | 568/864 |
| 4,429,147 | 1/1984 | Agnes et al. | 560/81 |
| 4,550,185 | 10/1985 | Mabry et al. | 549/508 |

FOREIGN PATENT DOCUMENTS 1037487 8/1978 Canada .
1512751 1/1976 United Kingdom .

OTHER PUBLICATIONS

Abu-Eishah, S. I., "Distillation Process for Separation of Homogeneous Binary Azeotropic Mixtures"–Dissertation, (1982).
Couteau et al., "Hydrogenation of dialkyl maleates or fumarates over Ba-stabilized Cu Chromite", Chemical Abstracts, p. 474, vol. 85, 1976.

*Primary Examiner*—Richard L. Raymond
*Attorney, Agent, or Firm*—Maria Tungol; William H. Magidson; Ralph C. Medhurst

[57] ABSTRACT

Mixtures of tetrahydrofuran and 1,4-butanediol at a predetermined mole ratio are produced by the hydrogenation of dimethylsuccinate in the presence of a copper chromite catalyst wherein said ratio is controlled by conducting the hydrogenation within a particular temperature range. Methanol is added to the ester feed to increase conversion and reduce transesterification. Tetrahydrofuran and 1,4-butanediol are separated from a mixture which also contains water and methanol by a series of distillations including a superatmospheric distillation.

13 Claims, No Drawings

COPRODUCTION OF BUTANEDIOL AND TETRAHYDROFURAN AND THEIR SUBSEQUENT SEPARATION FROM THE REACTION PRODUCT MIXTURE

This is a continuation-in-part of Ser. No. 710,016, filed on Mar. 11, 1985, now U.S. Pat. No. 4,613,707.

BACKGROUND OF THE INVENTION

This invention relates to the process for producing 1,4-butanediol and tetrahydrofuran by hydrogenation of dimethylsuccinate in the presence of a copper chromite catalyst wherein the temperature of the reaction is controlled to obtain a reaction product mixture with a predetermined mole ratio of 1,4-butanediol and tetrahydrofuran. This invention also relates to a method of separating 1,4-butanediol and tetrahydrofuran from a mixture containing other components such as methanol and water.

Tetrahydrofuran is a well-known solvent and an intermediate in the manufacture of 1,4-dichlorobutane, nylon, and polyurethanes. Dehydration of 1,4-butanediol produces tetrahydrofuran. Other reaction products from 1,4-butanediol include acetylenic chemicals such as gamma-butyrolactone, pyrrolidone, alkyl pyrrolidones, vinyl pyrrolidone, and poly-vinyl pyrrolidone. Butanediols are also useful in the production of polymeric materials such as polybutylene terephthalate. Almost all of the butanediol on the market today is obtained via butynediol which is produced from acetylene and formaldehyde by the Reppe synthesis. Another method of producing 1,4-butanediol is the hydrolysis of 1,4-dichlorobutene to 1,4-butenediol which is then hydrogenated to butanediol.

U.S. Pat. No. 2,772,291 and 2,772,292 describe the hydrogenation of maleic anhydride in the presence of nickel or cobalt catalysts to produce mixtures containing tetrahydrofuran. Neither patent discloses the use of copper chromite in the hydrogenation of a succinate ester. U.S. Pat. No. 2,772,293 also discloses a method of hydrogenating maleic anhydride to tetrahydrofuran using nickel or cobalt based catalysts. The patentees note that when the process was attempted with a copper chromite catalyst, conversion to tetrahydrofuran was not detected.

U.S. Pat. No. 4,301,077 discloses a process of hydrogenating oxygenated C4 hydrocarbons in the presence of water and a ruthenium-containing catalyst. Although tetrahydrofuran and 1,4-butanediol are obtained from the process, the use of a copper chromite catalyst is not disclosed.

U.S. Pat. No. 4,048,196 discloses the preparation of an intermediate, gamma-butyrolactone which is subsequently converted into butanediol and/or tetrahydrofuran using a nickel catalyst. British Patent No. 1,512,751 discloses the preparation of 1,4-butanediol from gamma-butyrolactone using a copper oxide, chromium oxide catalyst which has been pretreated with hydrogen. The process of this invention is a method of producing mixtures of tetrahydrofuran and 1,4-butanediol in a one-step reaction without the separate preparation of gamma-butyrolactone as an intermediate.

A multistage process for producing 1,4-butanediol from maleic anhydride is disclosed in U.S. Pat. No. 4,361,710. In contrast to the process of this invention, the process of the patent requires the washing of the mixture containing maleic anhydride with an aliphatic alcohol of not less than 8 carbon atoms with subsequent heating to form a solution of maleic diester in the alcohol. The production of tetrahydrofuran is also disclosed when the residence time of the reactants in the reactor is increased with the amount of tetrahydrofuran increasing up to 25% of the butanediol. The process of the present invention can produce mixtures in which the mole ratio of tetrahydrofuran to butanediol is greater than 2.

The hydrogenation of mono- and dialkyl esters is taught in U.S. Pat. No. 2,091,800. Dialkyl esters are hydrogenated using a copper chromite catalyst at 250° C. but there is no mention of tetrahydrofuran as a product of the reaction. In fact, the hydrogenation product of diethyl succinate at 250° C. is reported as tetramethylene glycol in a yield of 80.5%. Canadian Patent No. 1,037,487 discloses that tetrahydrofuran has been prepared from esters such as succinic acid esters by hydrogenation over a hydrogenation catalyst. However, the reference does not disclose any specific hydrogenation catalyst. One skilled in the art would not expect the copper chromite catalyst required in the process of this invention to produce tetrahydrofuran in any significant amounts in view of the patents previously cited. The process of this invention using dimethylsuccinate and a copper chromite catalyst can produce a significant amount of tetrahydrofuran depending upon the reaction temperature used.

U.S. Pat. No. 4,172,961 discloses a process for the production of 1,4-butanediol wherein a dialkyl alkoxy succinate-containing mixture is hydrogenated in the presence of a copper chromite catalyst to form a mixture comprising 1,4-butanediol and the corresponding alkanol. Among the by-products of the hydrogenation reaction are dibutylsuccinate, dibutylfumarate, 2-butoxy-1,4-butanediol and other higher molecular weight residues. Tetrahydrofuran is mentioned as a solvent but not as a product of the reaction.

U.S. Pat. No. 4,268,695 discloses a one-stage process for preparing butanediol by hydrogenating a solution of maleic anhydride in an alcohol in the presence of a copper chromite catalyst. Formation of small amounts of tetrahydrofuran is also disclosed but the yield of butanediol is said to be greater than 90 mole percent. Succinic esters are not disclosed as starting material but apparently appear among the by-products of the hydrogenation.

The separation of methanol from a mixture containing tetrahydrofuran, water and methanol using two columns at different pressures is disclosed in U.S. Pat. No. 4,332,645. The separation method of of the present invention is conducted with a greater amount of methanol. This is advantageous because the methanol/tetrahydrofuran azeotrope is easier to separate by superatmospheric distillation than the water/tetrahydrofuran azeotrope. Unlike the method of the patent, the separation method of the present invention results in complete purification of methanol because the methanol/tetrahydrofuran azeotrope taken overhead in the second tower is recycled to the first tower.

A one-step method of producing tetrahydrofuran and 1,4-butanediol from which significant amounts of either compound can be produced is more convenient and economical than a multi-step process which requires greater amounts of catalyst. Another advantage is the ability to efficiently vary the amounts of each material produced in response to market conditions or specific customer orders. The separation process is more efficient since the mixture of products is purified by one separation method.

The object of this invention is to provide a process of producing a mixture comprising tetrahydrofuran and 1,4-butanediol wherein the mole ratio of tetrahydrofuran to 1,4-butanediol is controlled by conducting the hydrogenation reaction within a particular temperature range. The presence of methanol during the reaction at the lower temperature range increases ester conversion and selectivity and reduces transesterification. A further object of this invention is a method of separating tetrahydrofuran and 1,4-butanediol from a mixture which also contains water and methanol.

SUMMARY OF THE INVENTION

Mixtures of tetrahydrofuran and 1,4-butanediol at a predetermined mole ratio are produced by the hydrogenation of dimethylsuccinate in the presence of a copper chromite catalyst wherein said ratio is controlled by conducting the hydrogenation within a particular temperature range. Methanol is added to the ester feed to increase conversion and reduce transesterification. Tetrahydrofuran and 1,4-butanediol are separated from a mixture which also contains water and methanol by a series of distillations including a superatmospheric distillation.

DESCRIPTION OF THE INVENTION

This invention is a process of producing a mixture comprising tetrahydrofuran and 1,4-butanediol by the hydrogenation of dimethylsuccinate in the presence of a copper chromite catalyst wherein the mole ratio of tetrahydrofuran to 1,4-butanediol is controlled by conducting the reaction in a particular temperature range. Methanol is added to the ester feed to increase conversion and reduce transesterification. Further, this invention includes a method of separating tetrahydrofuran and 1,4-butanediol from a mixture which also contains water and methanol.

Tetrahydrofuran and 1,4-butanediol are produced by contacting dimethylsuccinate with hydrogen at elevated temperature and pressure in the presence of a copper chromite catalyst. Reaction products of the hydrogenation are listed in Table 1 in order of increasing boiling points:

TABLE 1

| Product | Boiling Point (°C.) |
| --- | --- |
| Methanol | 65 |
| Tetrahydrofuran | 66 |
| Water | 100 |
| N—Butanol | 118 |
| Dimethylsuccinate | 200 |
| Gamma-Butyrolactone | 204 |
| 1,4-Butanediol | 230 |
| Methyl 4-Hydroxybutyrate | Heavy |
| Methyl-(4-Hydroxybutyl)succinate | Heavy |
| Bis-(4-Hydroxybutyl)succinate | Heavy |

The dimethylsuccinate used in the process of this invention is a known compound and can be prepared by several methods including the oxidative carbonylation of a hydrocarbon olefin with carbon monoxide and an aliphatic alcohol in the presence of oxygen. As discussed previously, the production of significant amounts of tetrahydrofuran using dimethylsuccinate and a copper chromate catalyst is unexpected in view of the prior art which would lead one to expect a product of primarily 1,4-butanediol from the hydrogenation of four carbon anhydrides and four carbon esters.

The process of this invention can be conducted in either the batch or continuous mode. Typical batch modes include slurry and fixed bed methods. Continuous modes include plug flow and trickle bed methods. A continuous process is preferred because the higher catalyst to succinate ester weight ratios permit greater conversion to tetrahydrofuran in the temperature ranges of this invention. The trickle bed method is particularly preferred because the high catalyst to feed ratio in a trickle bed reactor allows rapid hydrogenation and high selectivity. Also, the relatively low velocity of liquid reactant passing over catalyst promotes the production of tetrahydrofuran in the temperature ranges of this invention.

The hydrogenation reaction is conducted by treating the dimethylsuccinate with gaseous hydrogen wherein the hydrogen is introduced at a pressure of about 500 to about 5000 psi, preferably about 1000 to about 2500 psi. The reaction time is determined by the reaction mode used and the catalyst to succinate weight ratio. Typical reaction times can range from about 15 minutes to about 5 hours. In the continuous mode, the reaction times can range from about 5 minutes to about 1 hour, preferably from about 30 to 40 minutes. The pressure in the reactor is maintained at the pressure of the incoming hydrogen.

According to the process of this invention, the reaction temperature is used to control the mole ratio of tetrahydrofuran to 1,4-butanediol in the reaction product mixture. When the hydrogenation of dimethylsuccinate is performed at a temperature from about 170° to about 220° C., a mixture comprising tetrahydrofuran and 1,4-butanediol is produced wherein the mole ratio of tetrahydrofuran to 1,4-butanediol is from about 0.02 to about 0.50. A mixture comprising tetrahydrofuran and 1,4-butanediol wherein the mole ratio of tetrahydrofuran to 1,4-butanediol is greater than 0.5 up to about 10, preferably about 0.75 to about 2.0, is obtained when the hydrogenation is conducted at a temperature greater than about 220 to about 350° C., preferably about 230 to about 270° C.

It has also been observed that the addition of a methanol solvent in a hydrogenation performed at the lower temperature range increases the conversion of dimethylsuccinate and the selectivity of the reaction. As shown in Table 3, transesterification is significantly reduced when using a methanol solvent thus increasing the total amount of tetrahydrofuran and 1,4-butanediol produced in the reaction. The methanol is added to the feed in an amount sufficient to maintain the transesterification below about 50 wt. %. Typically, methanol is added to the feed in an amount of about 20 to about 70 wt. %, preferably about 30 to about 60 wt. %. The amount of methanol solvent can be varied to reduce the level of transesterification and to minimize the amount of methanol processed in the separation zone.

The copper chromite catalyst used in the process of this invention is the known copper chromite hydrogenation catalyst. Such catalysts are disclosed in U.S. Pat. No. 2,091,800 herein incorporated by reference. The catalyst can include other metals or metal oxides such as barium as promoters. The form of the copper chromite catalyst is not critical in the process of the invention. The catalyst is generally used as pellets or can also be used as a powder or as large chunks. Rapid hydrogenation and high selectivity are observed when a relatively high catalyst to succinate weight ratio is used in the reaction zone. Typically, the catalyst to succinate weight ratio is between about 1:100 to about 1000:1 in the reaction zone. In the preferred continuous mode, this weight ratio is preferably between about 1:5 to about 5:1 in the reaction zone.

Although hydrogenation of esters in the presence of copper chromite catalysts is disclosed in the previously cited patents, one skilled in the art would expect butanediol as the principal product when an alkyl ester is hydrogenated in the presence of a copper chromite catalyst. When the process of this invention is conducted at temperatures of 230° C. or more, the mole ratio of tetrahydrofuran to 1,4-butanediol increases from about 0.5 to about 2.2 at about 250° C. Such a result is completely unexpected from the teaching of U.S. Pat. No. 2,091,800 in which the hydrogenation of diethylsuccinate at 250° C. is reported to produce an 80.5% yield of tetramethyleneglycol.

The desired products, tetrahydrofuran and 1,4-butanediol must be separated from the reaction product mixture and purified for subsequent use. By-products of the hydrogenation reaction include water, monomethylsuccinate, gamma butyrolactone, n-butanol, and so-called heavies (higher boiling materials) such as methyl-4-hydroxybutyrate, methyl-(4-hydroxybutyl)-succinate and bis-(4-hydroxybutyl)succinate. It is also desirable to separate the solvent, e.g., methanol for recycle to the feed stream. When dimethylsuccinate is prepared by oxidative carbonylation using methanol with the subsequent hydrogenation of dimethylsuccinate to the desired products, the methanol can also be recycled to the oxidative carbonylation feed or to the reactor.

The separation method of this invention provides for the separation of tetrahydrofuran and 1,4-butanediol from the reaction product mixture. This method can also be applied to other reaction mixtures which contain tetrahydrofuran, 1,4-butanediol, water, and methanol. It can also be applied to a process in which crude butanediol is dehydrated to tetrahydrofuran.

Separations from the hydrogenation reactor effluent are relatively complex because of the number of components and the existence of azeotropes. The following table lists the more important azeotropes which are formed:

TABLE 2

| Components | Boiling Points (°C.) | Azeotropic Boiling Point (°C.) | Azeotropic Composition (wt %) |
|---|---|---|---|
| Methanol | 65 | 59.6 | 24% |
| Tetrahydrofuran | 66 | | 76% |
| Tetrahydrofuran | 65 | 63.8 | 95% |
| Water | 100 | | 5% |
| Water | 100 | 93.0 | 11.5% |
| Methyl-Butyrate | 102 | | 88.5% |
| Water | 100 | 82.7 | 44.5% |
| N—Butanol | 118 | | 55.5% |

The effluent is first fed into a distillation zone where the heavy fraction containing butanediol and higher boiling by-products is taken down for further processing to pure butanediol. The distillate from this zone contains methanol, tetrahydrofuran, water, n-butanol, gamma-butryrolactone and dimethylsuccinate (stream A). Stream A is then fed into a second distillation zone where methanol, tetrahydrofuran, water and n-butanol (stream B) are taken overhead and sent to subsequent distillation towers. The higher boiling components in the bottoms are recycled to the reactor.

Tetrahydrofuran forms azeotropes with both methanol and water. At atmospheric pressure, the composition of the tetrahydrofuran/methanol azeotrope is about 76 weight percent tetrahydrofuran and about 24 weight percent methanol. At 160 psig, the azeotropic composition shifts to about 30 weight percent tetrahydrofuran and about 70 weight percent methanol. At atmospheric pressure, the composition of the tetrahydrofuran/water azeotrope is about 95 weight percent tetrahydrofuran. At 100 psig, the azeotropic composition shifts to 88 weight percent tetrahydrofuran. Therefore, any tetrahydrofuran/methanol or tetrahydrofuran/water azeotrope redistilled at superatmospheric pressure will leave pure tetrahydrofuran in the bottoms. According to the process of this invention, this effect is used after the initial distillations by feeding stream B into a first tower to remove excess water and methanol. The resulting overhead containing tetrahydrofuran and methanol (stream C), is fed into a second tower where pure tetrahydrofuran is obtained in the bottoms. The second tower is operated at a pressure greater than the first tower to shift the weight percent in the tetrahydrofuran azeotrope so that essentially all of the methanol is taken overhead as an azeotrope with some tetrahydrofuran and recycled back to the first tower. The bottoms from the second tower are essentially anhydrous tetrahydrofuran.

The recycling of the methanol/tetrahydrofuran azeotrope from the second tower back to the feed to the first tower permits the recovery of pure methanol. Since the azeotropic ratio of methanol/tetrahydrofuran is less in the first tower, the excess methanol goes to the bottoms with water. The separation of methanol from water is easily performed and the methanol can be recycled to previous reaction steps.

In a more specific description of the separation process of this invention, the tetrahydrofuran/methanol azeotrope is separated from excess methanol and water in the first distillation tower. Any feed material which is higher boiling than water will exit the system with the water in the bottoms of the first tower. The methanol and water mixture in the bottoms of the first tower can be fed to a third tower where pure methanol is easily removed from the water and any other higher boiling materials for recycle to previous reactors. In the second tower, all of the methanol is taken overhead in the tetrahydrofuran azeotrope. Because the second tower is operated at the higher pressure, less tetrahydrofuran is taken overhead in the azeotrope when compared to the amount in the azeotrope from the first tower at lower pressure. Since all of the methanol is taken overhead in the azeotrope, pure tetrahydrofuran is isolated at the bottom of the second tower.

The distillation towers used in the process of this invention are known in the distillation art. The pressure in the first tower can be varied as desired and is preferably from about 0.5 to 2 atmospheres, preferably 1 atmosphere. The pressure in the second tower is greater than that of the first and can range from about 2 to about 20 atmospheres, preferably about 6 to about 12 atmospheres. The temperatures at which the azeotropes are taken overhead in each tower will be determined by the pressures chosen and the specific composition of the reaction product mixture. Appropriate pressures can be readily determined by one skilled in the art for convenient processing.

The following examples are given for the purpose of further illustrating the present invention and are not intended in any way to limit the scope of the invention.

EXAMPLE 1

Dimethylsuccinate was fed into a trickle bed reactor at a feed rate of about 30 grams per hour together with hydrogen gas at a pressure of 2,000 psig in the presence of 250 grams of barium promoted copper chromite (in the form of ⅛ inch pellets). The hydrogenation was conducted at 248° C. which resulted in 100 percent dimethylsuccinate conversion and a reaction product of which the mixture of tetrahydrofuran and 1,4-butanediol was 87.3 weight percent. The mole ratio of tetrahydrofuran to butanediol was about 2.2.

EXAMPLES 2-11

The procedure of Example 1 was performed using different temperatures and different amounts of methanol in the dimethylsuccinate feed. The following table summarizes the results obtained from the reactions.

TABLE 3

| Temperature (°C.) | Alcohol in Feed (wt. %) | DMS[1] Conversion | Transesterification[2] (wt. %) | Mole Ratio THF[3]/BDO[4] |
|---|---|---|---|---|
| 170 | 40 | 67.8 | 39.9 | 0.02 |
| 170 | 50 | 91.1 | 22.6 | 0.02 |
| 169 | 60 | 98.1 | 5.0 | 0.02 |
| 189 | 20 | 87.0 | 28.7 | 0.06 |
| 190 | 30 | 94.7 | 19.0 | 0.06 |
| 190 | 40 | 95.1 | 14.6 | 0.07 |
| 211 | 10 | 94.2 | 17.6 | 0.20 |
| 210 | 30 | 100.0 | 0.3 | 0.16 |
| 230 | 30 | 100.0 | 0.0 | 0.74 |
| 248 | 0 | 100.0 | 0.0 | 2.2 |

[1]Dimethylsuccinate
[2]Transesterification products include:
methyl-4-hydroxybutylsuccinate
bis-(4-hydroxybutyl) succinate
butanediol-disuccinate
[3]Tetrahydrofuran
[4]1,4-Butanediol As illustrated above, transesterification is significantly reduced when using a methanol solvent thus increasing the total amount of tetrahydrofuran and 1,4-butanediol produced in the reaction.

What is claimed is:

1. A process of producing a mixture comprising tetrahydrofuran and 1,4-butanediol wherein the mole ratio of tetrahydrofuran to 1,4-butanediol is from about 0.02 to about 0.50, said process comprising reacting dimethylsuccinate with hydrogen in the presence of a copper chromite catalyst at a temperature from about 170° C. to about 220° C.

2. The process of claim 1 wherein the reaction is conducted at in the presence of a solvent comprising methanol.

3. The process of claim 1 wherein said mixture comprises tetrahydrofuran, 1,4-butanediol, water and methanol.

4. The process of claim 3 wherein tetrahydrofuran and 1,4-butanediol are removed from said mixture by
    (1) feeding said mixture into a first distillation zone wherein the butanediol is separated from said mixture and the remaining components are taken overhead as stream A;
    (2) feeding stream A into a second distillation zone in which tetrahydrofuran, water and methanol are taken overhead as stream B;
    (3) feeding stream B into a first tower wherein stream C containing tetrahydrofuran and methanol is taken overhead;
    (4) feeding stream C into a second tower wherein methanol is taken overhead and pure tetrahydrofuran is in the bottoms;
    (5) recycling the overhead from the second tower to stream B prior to entry into the first tower, wherein the second tower is operated at a pressure greater than the first tower.

5. A process of producing a mixture comprising tetrahydrofuran and 1,4-butanediol wherein the mole ratio of tetrahydrofuran to 1,4-butanediol is greater than 0.50 up to about 10, said process comprising reacting dimethylsuccinate with hydrogen in the presence of a copper chromite catalyst at a temperature from about 220° to about 350° C.

6. The process of claim 5 wherein the reaction is conducted at a temperature from about 230° to about 270° C.

7. The process of claim 5 wherein said mixture comprises tetrahydrofuran, 1,4-butanediol, water and methanol.

8. The process of claim 7 wherein tetrahydrofuran and 1,4-butanediol are removed from said mixture by
    (1) feeding said mixture into a first distillation zone wherein the butanediol is separated from said mixture and the remaining components are taken overhead as stream A;
    (2) feeding stream A into a second distillation zone in which tetrahydrofuran, water and methanol are taken overhead as stream B;
    (3) feeding stream B into a first tower wherein stream C containing tetrahydrofuran and methanol is taken overhead;
    (4) feeding stream C into a second tower wherein methanol is taken overhead and pure tetrahydrofuran is in the bottoms;
    (5) recycling the overhead from the second tower to stream B prior to entry into the first tower
wherein the second tower is operated at a pressure greater than the first tower.

9. The process of claim 8 wherein said first tower is operated at a pressure of about 0.5 to about 2 atmospheres.

10. The process of claim 8 wherein said second tower is operated at a pressure of about 2 to about 20 atmospheres.

11. The process of claim 10 wherein said second tower is operated at a pressure of about 6 to about 12 atmospheres.

12. The process of claim 8 wherein said first tower is operated at 1 atmosphere and said second tower is operated at 7 atmospheres.

13. The process of claim 8 wherein the methanol present in the bottoms in the distillation of step 3) is separated from water in a subsequent distillation step.

* * * * *